United States Patent
Mutz et al.

(10) Patent No.: US 6,893,836 B2
(45) Date of Patent: May 17, 2005

(54) SPATIALLY DIRECTED EJECTION OF CELLS FROM A CARRIER FLUID

(75) Inventors: Mitchell W. Mutz, Palo Alto, CA (US); Richard N. Ellson, Palo Alto, CA (US)

(73) Assignee: Picoliter Inc., Sunnyvale, CA (US)

( * ) Notice: Subject to any disclaimer, the term of this patent is extended or adjusted under 35 U.S.C. 154(b) by 418 days.

(21) Appl. No.: 09/999,166

(22) Filed: Nov. 29, 2001

(65) Prior Publication Data

US 2002/0142286 A1 Oct. 3, 2002

Related U.S. Application Data

(63) Continuation-in-part of application No. 09/727,391, filed on Nov. 29, 2000, now abandoned.

(51) Int. Cl.$^7$ .................................................. C12Q 1/02
(52) U.S. Cl. ..................................... 435/29; 435/173.1
(58) Field of Search ............................. 435/29, 173.1, 435/173.9

(56) References Cited

U.S. PATENT DOCUMENTS

| | | | |
|---|---|---|---|
| 4,308,547 A | * 12/1981 | Lovelady et al. | ............. 347/46 |
| 4,500,707 A | 2/1985 | Caruthers et al. | |
| 5,041,849 A | 8/1991 | Quate et al. | |
| 5,436,327 A | 7/1995 | Southern et al. | |
| 5,506,141 A | 4/1996 | Weinreb et al. | |
| 5,700,637 A | 12/1997 | Southern et al. | |
| 5,798,779 A | 8/1998 | Nakayasu et al. | |
| 5,900,361 A | 5/1999 | Klebe | |
| 6,044,981 A | 4/2000 | Chu et al. | |
| 6,103,479 A | 8/2000 | Taylor | |
| 6,106,599 A | * 8/2000 | Breton et al. | ............. 106/31.29 |
| 6,126,014 A | * 10/2000 | Gray et al. | ................. 209/163 |
| 6,416,164 B1 | * 7/2002 | Stearns et al. | ................. 347/46 |
| 6,467,877 B2 | * 10/2002 | Ellson | ......................... 347/46 |
| 6,603,118 B2 | * 8/2003 | Ellson et al. | ................ 250/288 |
| 6,610,223 B2 | * 8/2003 | Lee | ............................ 264/9 |
| 6,612,686 B2 | * 9/2003 | Mutz et al. | .................... 347/46 |
| 6,642,061 B2 | * 11/2003 | Ellson et al. | ................ 436/180 |
| 6,666,541 B2 | * 12/2003 | Ellson et al. | ................. 347/46 |
| 2002/0037375 A1 | 3/2002 | Ellson et al. | |
| 2002/0037527 A1 | 3/2002 | Ellson et al. | |

FOREIGN PATENT DOCUMENTS

| | | |
|---|---|---|
| EP | 0801305 A1 | 10/1997 |
| EP | 0845357 A2 | 6/1998 |
| WO | WO 92/18608 | 10/1992 |
| WO | WO 94/27142 | 11/1994 |
| WO | WO 97/45730 | 12/1997 |
| WO | WO 01/35071 A2 | 5/2001 |
| WO | WO 02/24324 | 3/2002 |

OTHER PUBLICATIONS

Coakley W. Ultrasonic Separations in Analytical Biotechnology. Trends in Biotechnology 15(12)506–511, 1997.*
U.S. patent application Ser. No. 09/669,194, Ellson et al., filed Sep. 25, 2000.
O'Donnell–Maloney et al. (1996), "Microfabrication and Array Technologies for DNA Sequencing and Diagnostics," *Genetic Analysis Biomolecular Engineering* 13:151–157.
Amemiya et al. (1997), *Proceedings of the 1997 IS&T's NIP 13: 1997 International Conference on Digital Printing Technologies*, pp. 698–702.
Matteuci et al. (1980), "The Synthesis of Oligodeoxypyrimidines on a Polymer Support," *Tetrahedron Letters* 21:719–722.
Steel et al. (2000), "The Flow–Thru Chip™: A Three–Dimensional Biochip Platform," *Microarray Biochip Technology*, Chapter 5, pp. 87–117, BioTechniques Books, Natick, MA.
U.S. patent application Ser. No. 09/669,996, Ellson et al., filed Sep. 25, 2000.
U.S. patent application Ser. No. 09/962,731, Ellson, filed Sep. 24, 2001.
U.S. patent application Ser. No. 09/963,173, Mutz et al., filed Sep. 25, 2001.
U.S. patent application Ser. No. 09/964,193, Mutz et al., filed Sep. 25, 2001.
U.S. patent application Ser. No. 09/964,212, Ellson et al., filed Sep. 25, 2001.

* cited by examiner

Primary Examiner—Ralph Gitomer
(74) Attorney, Agent, or Firm—Dianne E. Reed; Karen Canaan; Reed & Eberle LLP

(57) ABSTRACT

This invention is directed to the use of focused energy, particularly focused acoustic energy, in the spatially directed ejection of cells suspended in a carrier fluid, e.g., for providing a pattern of cells on a substrate surface, such as a cellular array.

6 Claims, 9 Drawing Sheets

SPATIALLY DIRECTED EJECTION OF CELLS FROM A CARRIER FLUID

CROSS-REFERENCE TO RELATED APPLICATIONS

This application is a CIP of application No. 09/727,391 filed Nov. 29, 2000, now abandoned.

TECHNICAL FIELD

This invention relates generally to the ejection of cells from a fluid, for example, onto a substrate surface to form a cellular array. More particularly, the invention relates to the use of focused acoustic energy to effect the spatially directed ejection of cells suspended in a carrier fluid. The invention additionally relates to the use of such a method for depositing cells onto a substrate surface, such as to form a patterned array of cells thereon.

BACKGROUND

Arrays of single living cells have been made by inserting individual cells into individual well sites or holes that are open on both the top and bottom, with the top opening large enough for a desired cell to pass through and the bottom opening too small for the desired cell to pass through (Weinreb et al., U.S. Pat. No. 5,506,141). The diameters of eukaryotic cells are greater than about 10 $\mu$m and those of the smallest prokaryotic cells, genus *Mycoplasma*, are about 0.15–0.30 $\mu$m; microfabrication techniques for manufacturing arrays of well sites or holes to accommodate cells of these diameters are well known (for example, Chu et al. in U.S. Pat. No. 6,044,981 teach methods for making holes or channels having dimensions as small as about 5 nanometers (nm) by employing a sacrificial layer; these dimensions are smaller than the resolution limit of photolithography, currently 350 nm). No currently employed methods of manipulating cells permit making an ordered array of single cells on a planar substrate surface. Further, no method of sorting cells into individual array sites by size exists other than that of controlling physical hole or well size as described by Weinreb et al., supra, to permit cell populations of differing size to enter and be contained in non-planar holes or wells.

The screening of cells is appreciated to initially require a relatively large known number of individual cells (as described for example by Weinreb et al., U.S. Pat. No. 5,506,141), to ensure detection of a particular cell function or characteristic among a population of cells at different life cycle stages and varying in other characteristics. It is also appreciated that the simultaneous delivery of screening and other reagents requires a fluidic nexus between each cell container and its nearest neighbors. Taylor, U.S. Pat. No. 6,103,479, describes a miniaturized cell array method and device for screening cells, comprising cells in physical wells that are microfluidically connected to independent reagent sources by microchannels that can supply fluid reagents to individual or multiple cells arrayed in the physical wells. Such systems may be easily altered to permit tests on individual cells or a large number of cells simultaneously, but they require costly and detailed microfabrication. The site density of such arrays is limited by the need to make individual wells according to demanding physical specifications, such as minimum well wall thickness for physical integrity and additional space for the channels themselves. Thus a need exists for maximizing site density while maintaining high flexibility for assaying populations and subpopulations, as well as for reducing microfabrication time, expense, and cost. A further need exists for microfluidic delivery of reagents to arrayed cells, whether or not contained in physical wells or localized on a planar substrate in virtual wells, without requiring either a corresponding array or individual microfabricated channels to supply each site with a desired reagent.

No method or device is known to exist for manipulating individual cells by ejecting them from a fluid onto a substrate surface without killing the cells. Thus a need exists for a method and corresponding device for ejecting a single cell from a fluid to a chosen surface locale or region, to permit selective ejection for patterning of cells on a surface. Such selective ejection can be used for making arrays and for other applications requiring cell pattering on a surface, such as engineering tissues and the like, or simply for sorting cells.

SUMMARY OF THE INVENTION

Accordingly, it is an object of the present invention to provide devices and methods that overcome the above-mentioned disadvantages of the prior art.

In one aspect of the invention, a method is provided for acoustically ejecting a plurality of fluid droplets, each containing a single cell, toward designated sites on a substrate surface, for deposition on the substrate surface, using a device such as that described in U.S. patent application Ser. No. 09/964,212 ("Acoustic Ejection of Fluids from a Plurality of Reservoirs"), inventors Ellson, Foote, and Mutz, filed on Sep. 25, 2001, and assigned to Picoliter, Inc. (Mountain View, Calif.).

As described in the aforementioned patent application, the device enables acoustic ejection of a plurality of fluid droplets toward designated sites on a substrate surface for deposition thereon. Such devices comprise: a plurality of cell containers or reservoirs each adapted to contain a fluid capable of carrying, for example, cells suspended therein; an acoustic ejector for generating acoustic radiation and a focusing means for focusing it at a focal point near the fluid surface in each of the reservoirs; and a means for positioning the ejector in acoustic coupling relationship to each of the cell containers or reservoirs. Preferably, each of the containers is removable, or comprised of an individual well in a well plate, and/or arranged in an array. In addition, the cell containers or reservoirs preferably: are substantially acoustically indistinguishable from one another, have appropriate acoustic impedance to allow the energetically efficient focusing of acoustic energy near the surface of a contained fluid, and are capable of withstanding conditions of the fluid-containing reagent.

In another aspect of the invention, an array of cells is provided on a substrate surface comprising an array of substantially planar sites, wherein each site contains a single cell. The array is prepared by positioning an acoustic ejector so as to be in an acoustically coupled relationship with a first cell suspension-containing reservoir containing a suspension of one cell type or clone, or a mixture of cell types or clones, in a first carrier fluid. After acoustic detection of the presence of a cell sufficiently close to the fluid surface, and detection of any properties used as criteria for ejection, the ejector is activated to generate and direct acoustic radiation so as to have a focal point within the carrier fluid and near the surface thereof and an energy sufficient to eject a droplet of carrier fluid having a volume capable of containing a single cell, thereby ejecting a single cell contained in a fluid droplet toward a first designated site on the substrate surface. Additional cells may be ejected from the first container. Alternatively, the ejector may be repositioned so as to be in an acoustically coupled relationship with a second cell suspension-containing reservoir and the process is repeated as above to eject a single cell contained in a droplet of the second fluid toward a second designated site on the substrate surface, wherein the first and second designated sites may or may not be the same. If desired, the method may be repeated with a plurality of cells from each container, with each reservoir generally although not necessarily containing a suspension of different cells or cell mixtures. The acoustic ejector is thus repeatedly repositioned so as to eject a single-cell-containing droplet from each reservoir toward a different designated site on a substrate surface. In such a way, the method is readily adapted for use in generating an array of cells on a substrate surface. The arrayed cells may be attached to the substrate surface by one or more external-marker-moiety/cognate-moiety-specific binding systems. An example of one such specific binding system is that using streptavidin as an external marker (effected by transformation), with biotin as the cognate moiety. Multiple specific binding systems include those using externally displayed IgM clones and epitopes as the cognate moiety.

In another aspect, useful for cell screening, the invention relates to a method for ejecting fluids from fluid reservoirs toward designated sites on a substrate surface where live cells reside. This aspect of the invention relates to a method for the systematic screening of cell arrays by channel-less microfluidic delivery using acoustic ejection, or parallel screening of all sites simultaneously effected by immersion of the whole array in a reagent. In another aspect of the invention, a system for making, screening, and characterizing live cell arrays is provided.

In yet another aspect, the invention provides a method of forming arrays of single live cells more rapidly, flexibly, and economically than by approaches requiring the use of holes or physical wells together with independent channel-based microfluidic delivery.

Yet another aspect of the invention provides relatively high-density arrays of live cells, e.g. having a higher density than attainable by approaches requiring the use of holes or physical wells together with independent channel-based microfluidic delivery.

Yet another aspect of the invention provides ejection of selected live cells from a fluid.

A final aspect of the invention provides general spatial patterning of cells on a surface with or without a specific attachment system.

BRIEF DESCRIPTION OF THE DRAWINGS

FIG. 1 is not to scale, and certain dimensions may be exaggerated for clarity of presentation. FIG. 1A shows the acoustic ejector acoustically coupled to the first cell container or reservoir and activated in order to eject a droplet of fluid containing a single cell from within the first cell container or reservoir toward a designated site on a substrate surface. FIG. 1B shows the acoustic ejector acoustically coupled to a second cell container or reservoir.

FIG. 2A is a schematic top plane view of the two well plates, i.e., the cell container or reservoir well plate and the substrate surface having arrayed cells contained in fluid droplets. FIG. 2B illustrates in cross-sectional view a device comprising the cell container or reservoir well plate of FIG. 2A acoustically coupled to an acoustic ejector, wherein a cell contained in a droplet is ejected from a first well of the cell container or reservoir well plate into a first well of the substrate well plate. FIG. 2C illustrates in cross-sectional view the device illustrated in FIG. 2B, wherein the acoustic ejector is acoustically coupled to a second well of the cell container or reservoir well plate and further wherein the device is aligned to enable the acoustic ejector to eject a droplet from the second well of the cell container or reservoir well plate to a second well of the substrate well plate.

FIG. 3A illustrates the ejection of a cell-containing fluid droplet onto a designated site of a substrate surface. FIG. 3B illustrates the ejection of a droplet containing a first cell displaying a first marker moiety adapted for attachment to a modified substrate surface. FIG. 3C illustrates the ejection of a droplet of a second fluid containing a second molecular moiety adapted for attachment to the first molecule. FIG. 3D illustrates the substrate and the dimer synthesized in situ by the process illustrated in FIGS. 3A, 3B, and 3C.

FIG. 4A illustrates two different cells resident at adjacent array sites, contained in fluid droplets adhering to a designated site of a substrate surface by surface tension, with each cell further attached to the site by binding of streptavidin (SA) to a biotinylated (biotin (B) linked) surface. Streptavidin is displayed on the cell exterior as a result of transformation by a genetic coding sequence for external-display-targeted streptavidin. FIG. 4B illustrates two different cells resident at adjacent array sites, contained in fluid droplets adhering to a designated site of a substrate surface by surface tension, with each cell further attached to the site by binding of two externally displayed antigenic epitopes characteristic of the cell (here E1 and E2) to two different monoclonal antibodies (mAb-E1, mAb-E2), specific respectively for the different epitopes, each mAb linked to the surface at only one of the adjacent array sites.

FIGS. 5A and 5B illustrate the device schematically. FIG. 5C illustrates a top view of channels containing live cells, with the substrate surface having arrayed cells contained in fluid droplets.

DETAILED DESCRIPTION OF THE INVENTION

Figure 1A:
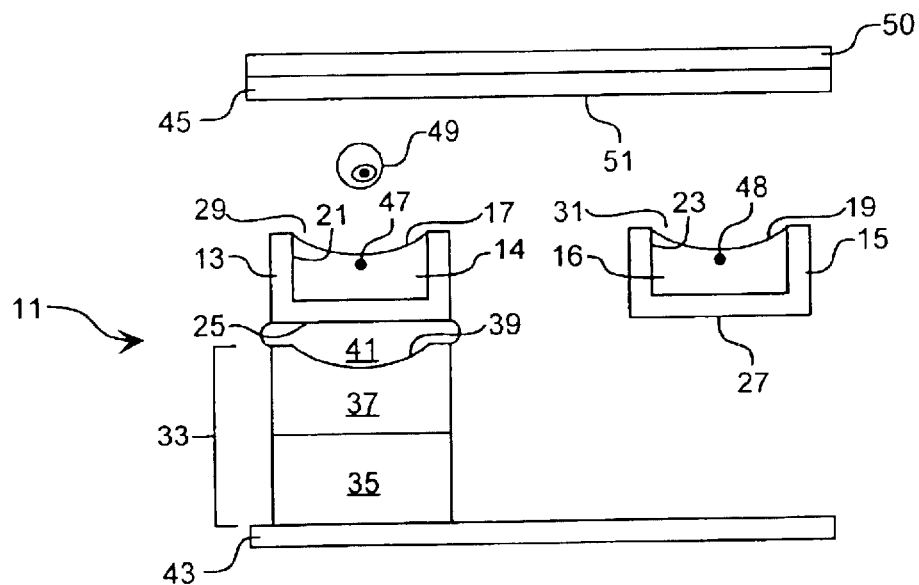
FIGS. 1A and 1B, collectively referred to as FIG. 1, schematically illustrate in simplified cross-sectional view an embodiment of a device useful in conjunction with the invention, the device comprising first and second cell containers or reservoirs, an acoustic ejector, and an ejector positioning means. As with all figures referenced herein, in which like parts are referenced by like numerals.

Before describing the present invention in detail, it is to be understood that this invention is not limited to specific fluids, biomolecules, or device structures, as such may vary. It is also to be understood that the terminology used herein is for the purpose of describing particular embodiments only, and is not intended to be limiting.

It must be noted that, as used in this specification and the appended claims, the singular forms "a," "an," and "the" include plural referents unless the context clearly dictates otherwise. Thus, for example, reference to "a cell container" or "a reservoir" includes a single cell container or reservoir as well as a plurality of cell containers or reservoirs, reference to "a fluid" includes a single fluid or a combination and/or mixture of different fluids, reference to "a biomolecule" includes a single molecule as well as a combination and/or mixture of biomolecules, and the like.

In describing and claiming the present invention, the following terminology will be used in accordance with the definitions set out below.

The terms "acoustic coupling" and "acoustically coupled" used herein refer to a state wherein an object is placed in direct or indirect contact with another object so as to allow acoustic radiation to be transferred between the objects without substantial loss of acoustic energy. When two entities are indirectly acoustically coupled, an "acoustic coupling medium" is needed to provide an intermediary through which acoustic radiation may be transmitted. Thus, an ejector may be acoustically coupled to a fluid, e.g., by immersing the ejector in the fluid or by interposing an acoustic coupling medium between the ejector and the fluid to transfer acoustic radiation generated by the ejector through the acoustic coupling medium and into the fluid.

The term "bound," as in, for example, a substrate surface having a cell "bound" thereto, includes covalent binding, adsorption, and physical immobilization. The terms "attached," binding" and "bound" are identical in meaning to the term "attached."The term "adsorb" as used herein refers to the noncovalent retention of a molecule, molecular segment, or cell by a substrate surface. That is, adsorption occurs as a result of noncovalent interaction between a substrate surface and adsorbing moieties present on the entity that is adsorbed. Adsorption may occur through hydrogen bonding, van der Waal's forces, polar attraction or electrostatic forces (i.e., through ionic bonding). Often the substrate may be functionalized with adsorbent moieties to interact in a certain manner.

The term "array" used herein refers to a two-dimensional arrangement of features or materials, e.g., cells. Arrays are generally comprised of regular, ordered features, as in, for example, a rectilinear grid, parallel stripes, spirals, and the like, but non-ordered arrays may be advantageously used as well.

The terms "library" and "combinatorial library" are used interchangeably herein to refer to a plurality of chemical or biological moieties present on the surface of a substrate, wherein each moiety is different from each other moiety. The moieties may be, e.g., peptidic molecules and/or oligonucleotides.

The term "fluid" as used herein refers to matter that is nonsolid or at least partially gaseous and/or liquid. A fluid may contain a solid that is minimally, partially, or fully solvated, dispersed, or suspended; particles comprised of gels or discrete fluids may also be suspended in a fluid. Examples of fluids include, without limitation, aqueous liquids (including water per se and salt water) and nonaqueous liquids such as organic solvents and the like. Live cells suspended in a carrier fluid represent an example of a gel or discrete fluid suspended in a fluid.

The term "near" is used to refer to the distance from the focal point of the focused acoustic radiation to the surface of the fluid from which a droplet is to be ejected. The distance should be such that the focused acoustic radiation directed into the fluid results in droplet ejection from the fluid surface, and one of ordinary skill in the art will be able to select an appropriate distance for any given fluid using straightforward and routine experimentation. Generally, however, a suitable distance between the focal point of the acoustic radiation and the fluid surface is in the range of about 1 to about 15 times the wavelength of the speed of sound in the fluid, more typically in the range of about 1 to about 10 times that wavelength, preferably in the range of about 1 to about 5 times that wavelength.

The terms "focusing means" and "acoustic focusing means" refer to a means for causing acoustic waves to converge at a focal point by either a device separate from the acoustic energy source that acts like an optical lens, or by the spatial arrangement of acoustic energy sources to effect convergence of acoustic energy at a focal point by constructive and destructive interference. A focusing means may be as simple as a solid member having a curved surface, or it may include complex structures such as those found in Fresnel lenses, which employ diffraction in order to direct acoustic radiation. Suitable focusing means also include phased array methods as known in the art and described, for example, in U.S. Pat. No. 5,798,779 to Nakayasu et al. and Amemiya et al. (1997) *Proceedings of the 1997 IS&T NIP13 International Conference on Digital Printing Technologies Proceedings*, at pp. 698–702.

The term "reservoir" as used herein refers to a receptacle or chamber for holding or containing a fluid. Thus, a fluid in a reservoir necessarily has a free surface, i.e., a surface that allows a droplet to be ejected therefrom. As long as a fluid container has at least one free surface from which fluid can be ejected, the container is a reservoir regardless of specific geometry. Thus a "reservoir" includes, for example, a microfluidic channel containing flowing fluid from which droplets are ejected. A "cell container" or "cell reservoir" is a reservoir that is specialized for ejection of living cells suspended in a carrier fluid, and includes, by example, a microfluidic or other channel through which living cells flow suspended in a carrier fluid.

The term "substrate" as used herein refers to any material having a surface onto which one or more fluids may be deposited. The substrate may be constructed in any of a number of forms such as wafers, slides, well plates, membranes, for example. In addition, the substrate may be porous or nonporous as may be required for deposition of a particular fluid. Suitable substrate materials include, but are not limited to, supports that are typically used for solid phase chemical synthesis, e.g., polymeric materials (e.g., polystyrene, polyvinyl acetate, polyvinyl chloride, polyvinyl pyrrolidone, polyacrylonitrile, polyacrylamide, polymethyl methacrylate, polytetrafluoroethylene, polyethylene, polypropylene, polyvinylidene fluoride, polycarbonate, divinylbenzene styrene-based polymers), agarose (e.g., Sepharose®), dextran (e.g., Sephadex®), cellulosic polymers and other polysaccharides, silica and silica-based materials, glass (particularly controlled pore glass, or "CPG") and functionalized glasses, ceramics, and such substrates treated with surface coatings, e.g., with microporous polymers (particularly cellulosic polymers such as nitrocellulose), microporous metallic compounds (particularly microporous aluminum), antibody-binding proteins (available from Pierce Chemical Co., Rockford Ill.), bisphenol A polycarbonate, or the like. Porous substrates of particular interest include, without limitation: uncoated porous glass slides, including CPG slides; porous glass slides coated with a polymeric coating, e.g., an aminosilane or poly-L-lysine coating, thus having a porous polymeric surface; and nonporous glass slides coated with a porous coating. The porous coating may be a porous polymer coating, such as may be comprised of a cellulosic polymer (e.g., nitrocellulose) or polyacrylamide, or a porous metallic coating (for example, comprised of microporous aluminum). Examples of commercially available substrates having porous surfaces include the Fluorescent Array Surface Technology (FAST™) slides available from Schleicher & Schuell, Inc. (Keene, N.H.), which are coated with a 10–30 $\mu$m thick porous, fluid-permeable nitrocellulose layer that substantially increases the available binding area per unit area of surface. Other commercially available porous substrates include the CREATIVECHIP® permeable slides currently available from Eppendorf AG (Hamburg, Germany), and substrates having "three-dimensional" geometry, by virtue of an ordered, highly porous structure that enables reagents to flow into and penetrate through the pores and channels of the entire structure. Such substrates are available from Gene Logic, Inc. under the tradename "Flow-Thru Chip," and are described by Steel et al. in Chapter 5 of *Microarray Biochip Technology* (BioTechniques Books, Natick, Mass., 2000).

The term "porous" as in a "porous substrate" or a "substrate having a porous surface," refers to a substrate or surface, respectively, having a porosity (void percentage) in the range of about 1% to about 99%, preferably about 5% to about 99%, more preferably in the range of about 15% to about 95%, and an average pore size of about 100 Å to about 1 mm, typically about 500 Å to about 0.5 mm.

The term "impermeable" is used in the conventional sense to mean not permitting water or other fluid to pass through. The term "permeable" as used herein means not "impermeable." Thus, a "permeable substrate" and a "substrate having a permeable surface" refer to a substrate or surface, respectively, which can be permeated with water or other fluid.

While the foregoing support materials are representative of conventionally used substrates, it is to be understood that a substrate may in fact comprise any biological, nonbiological, organic and/or inorganic material, and may be in any of a variety of physical forms, e.g., particles, strands, precipitates, gels, sheets, tubing, spheres, containers, capillaries, pads, slices, films, plates, and the like, and may further have any desired shape, such as a disc, square, sphere, circle, etc. The substrate surface may or may not be flat, e.g., the surface may contain raised or depressed regions. A substrate may additionally contain or be derivatized to contain reactive functionalities. These are widely known and include, for example, silicon dioxide supports containing reactive Si—OH groups, polyacrylamide supports, polystyrene supports, polyethylene glycol supports, and the like.

The term "surface modification" as used herein refers to the chemical and/or physical alteration of a surface by an additive or subtractive process to change one or more chemical and/or physical properties of a substrate surface or a selected site or region of a substrate surface. For example, surface modification may involve (1) changing the wetting properties of a surface, (2) functionalizing a surface, i.e., providing, modifying or substituting surface functional groups, (3) defunctionalizing a surface, i.e., removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface. Any of the substrate surfaces herein may be modified in one or more of the foregoing ways, and the term "surface" is intended to include modified surfaces as just described. "Optional" or "optionally" means that the subsequently described circumstance may or may not occur, so that the description includes instances where the circumstance occurs and instances where it does not.

The term "substantially" as in, for example, the phrase "substantially all cells of an array," refers to at least 90%, preferably at least 95%, more preferably at least 99%, and most preferably at least 99.9%, of the cells of an array. Other uses of the term "substantially" involve an analogous definition.

In one embodiment, then, the invention pertains to a device for acoustically ejecting a plurality of single-cell-containing droplets toward designated sites on a substrate surface. The device comprises: a plurality of cell containers or reservoirs, each adapted to contain a carrier fluid within which living cells are suspended; an ejector comprising an acoustic radiation generator for generating acoustic radiation; a focusing means for focusing acoustic radiation at a focal point within and near the fluid surface in each of the reservoirs; and a means for positioning the ejector in acoustic coupling relationship to each of the reservoirs.

FIGS. 1 and 5 illustrate alternative embodiments of the employed device in simplified cross-sectional view. FIG. 1 depicts a cell ejection system where the cell container or reservoir is a conventional container, such as a conventional petri dish, which is radially symmetrical. In FIG. 5, the cell reservoir is a fluidic channel, through which live cells flow in a carrier fluid. The device 11 includes a plurality of cell containers or reservoirs, i.e., at least two containers or reservoirs, with a first cell container indicated at 13 and a second container indicated at 15, each adapted to contain a fluid in which live cells are suspended, and each fluid having a fluid surface; e.g., a first cell container having cells suspended in fluid 14 and a second cell container having cells suspended in fluid 16, with fluid surfaces respectively indicated at 17 and 19. The suspended cells and carrier fluids of 14 and 16 may be the same or different. As depicted, the cell containers or reservoirs are of substantially identical construction so as to be substantially acoustically indistinguishable, but identical construction is not a requirement. The cell containers are shown as separate removable components but may, if desired, be fixed within a plate or other substrate. For example, the plurality of containers in FIG. 1 may comprise individual wells in a well plate, optimally although not necessarily arranged in an array. Likewise, the plurality of containers in FIG. 5 may comprise separate channels or individual channels in a plate, for example a pattern of individual microfluidic channels etched into a plate as by photolithography. Each of the cell containers or reservoirs 13 and 15 is preferably bilaterally (FIG. 5B channels) or axially (FIG. 1) symmetric. They each have substantially vertical walls 21 and 23 that extend upward from reservoir bases 25 and 27 and terminate at openings 29 and 31, respectively, although other reservoir shapes may be used, including those with enclosed fluidic channels that have an aperture or opening for ejection at a specific location. The material and thickness of each cell container or reservoir base should be such that acoustic radiation may be transmitted therethrough and into the fluid contained within the reservoir.

The device embodiments depicted in FIGS. 1 and 5 also include an acoustic ejector 33 comprised of an acoustic radiation generator 35 for generating acoustic radiation, and a focusing means 37 for focusing the acoustic radiation at a focal point within the fluid from which a droplet is to be ejected, near the fluid surface. As shown in FIGS. 1 and 5, the focusing means 37 may comprise a single solid piece having a concave surface 39 for focusing acoustic radiation, but the focusing means may be constructed in other ways as discussed below. The acoustic ejector 33 is thus adapted to generate and focus acoustic radiation so as to eject a droplet of fluid from each of the fluid surfaces 17 and 19 when acoustically coupled to reservoirs 13 and 15, and thus to fluids 14 and 16, respectively. The acoustic radiation generator 35 and the focusing means 37 may function as a single unit controlled by a single controller, or they may be independently controlled, depending on the desired performance of the device. Typically, single ejector designs are preferred over multiple ejector designs, because accuracy of droplet placement and consistency in droplet size and velocity are more easily achieved with a single ejector.

As will be appreciated by those skilled in the art, any of a variety of focusing means may be employed in conjunction with the present invention. For example, one or more curved surfaces may be used to direct acoustic radiation to a focal point near a fluid surface. One such technique is described in U.S. Pat. No. 4,308,547 to Lovelady et al. Focusing means with a curved surface have been incorporated into commercially available acoustic transducers such as those manufactured by Panametrics Inc. (Waltham, Mass.). In addition, Fresnel lenses are known in the art for directing acoustic energy at a predetermined focal distance from an object plane. See, e.g., U.S. Pat. No. 5,041,849 to Quate et al. Fresnel lenses may have a radial phase profile that diffracts a substantial portion of acoustic energy into a predetermined diffraction order at diffraction angles that vary radially with respect to the lens. The diffraction angles should be selected to focus the acoustic energy within the diffraction order on a desired object plane. Phased arrays of acoustic energy emitters have also been used to focus acoustic energy at a specified point as a result of constructive and destructive interference between the acoustic waves emitted by the arrayed sources (Amemiya et al. (1997) Proceedings of 1997 IS&T NIP13 International Conference on Digital Printing Technologies, pp. 698–702.).

There are also a number of ways to acoustically couple the ejector 33 to each individual reservoir and thus to the fluid therein. One such approach is through direct contact, as is described, for example, in U.S. Pat. No. 4,308,547 to Lovelady et al., wherein a focusing means constructed from a hemispherical crystal having segmented electrodes is submerged in a liquid to be ejected. The aforementioned patent further discloses that the focusing means may be positioned at or below the surface of the liquid. This approach for acoustically coupling the focusing means to a fluid is undesirable, however, when the ejector is used to eject different fluids from a plurality of containers or reservoirs, as repeated cleaning of the focusing means would be required in order to avoid cross-contamination. The cleaning process would necessarily lengthen the transition time between each droplet ejection event. In addition, in such a method, cells in the fluid would adhere to the ejector as it is removed from a container, wasting cellular material that may be rare or irreplaceable. Finally, submersion in the fluid is not possible with conventional acoustic energy focusing means when the reservoirs are microfabricated, as when the cell containers are microfluidic channels or microwells, because of the containers being too small.

One of skill in the art of microfabrication would be able to make a focusing means comprising a microfabricated, curved member. Similarly, a microfabricated focusing means constructed from a hemispherical crystal having segmented electrodes, e.g. a miniature focusing means as described in U.S. Pat. No. 4,308,547 to Lovelady et al., can be made by routine microfabrication techniques. Submersion would then be possible with the same disadvantages as above. For microfluidic channels or wells, then, a focusing means as well as a source of acoustic energy could be integrated into the microfabricated assembly.

An approach practicable for any reservoir dimensions would be to acoustically couple a conventional non-microfabricated or macro-scale ejector to the reservoirs and reservoir fluids without bringing any portion of the ejector, e.g., the focusing means, into contact with any of the fluids to be ejected. To this end, the present invention provides an ejector positioning means for positioning the ejector in controlled and repeatable acoustic coupling with each of the fluids in the cell containers or reservoirs to eject droplets therefrom without submerging the ejector therein. This method typically involves direct or indirect contact between the ejector and the external surface of each reservoir. When direct contact is used in order to acoustically couple the ejector to each reservoir, it is preferred that the direct contact is wholly conformal to ensure efficient acoustic energy transfer. That is, the ejector and the reservoir should have corresponding surfaces adapted for mating contact. Thus, if acoustic coupling is achieved between the ejector and reservoir through the focusing means, it is desirable for the reservoir to have an outside surface that corresponds to the surface profile of the focusing means. Without conformal contact, efficiency and accuracy of acoustic energy transfer may be compromised. In addition, since many focusing means have a curved surface, the direct contact approach may necessitate the use of reservoirs having a specially formed inverse surface.

Figure 5A:
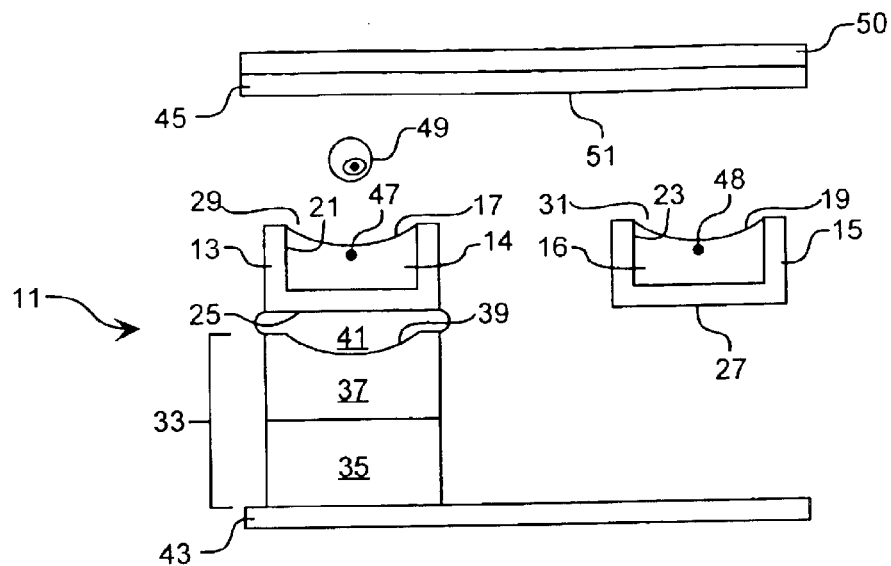
FIGS. 5A, 5B, and 5C, collectively referred to as FIG. 5, depict a device having a fluidic channel as the container from which the cells are ejected onto the substrate.

Optimally, acoustic coupling is achieved between the ejector and each of the reservoirs through indirect contact, as illustrated in FIGS. 1A and 5A. In the figures, an acoustic coupling medium 41 is placed between the ejector 33 and the base 25 of reservoir 13, with the ejector and reservoir located at a predetermined distance from each other. The acoustic coupling medium may be an acoustic coupling fluid, preferably an acoustically homogeneous material in conformal contact with both the acoustic focusing means 37 and each reservoir. In addition, it is important to ensure that the fluid medium is substantially free of material having different acoustic properties than the fluid medium itself. As shown, the first reservoir 13 is acoustically coupled to the acoustic focusing means 37 such that an acoustic wave is generated by the acoustic radiation generator and directed by the focusing means 37 into the acoustic coupling medium 41, which then transmits the acoustic radiation into the reservoir 13.

In operation, reservoirs 13 and 15 of the device are each filled with first and second carrier fluids having cells or cell mixtures 14 and 16 suspended therein, respectively, as shown in FIGS. 1 and 5. The acoustic ejector 33 is positionable by means of ejector positioning means 43, shown below reservoir 13, in order to achieve acoustic coupling between the ejector and the reservoir through acoustic coupling medium 41. Substrate 45 is positioned above and in proximity to the first reservoir 13 such that one surface of the substrate, shown in FIGS. 1 and 5 as underside surface 51, faces the reservoir and is substantially parallel to the surface 17 of the fluid 14 therein. Once the ejector, the reservoir, and the substrate are in proper alignment, the acoustic radiation generator 35 is activated to produce acoustic radiation that is directed by the focusing means 37 to a focal point 47 near the fluid surface 17 of the first reservoir. As a result, droplet 49 is ejected from the fluid surface 17 onto a designated site on the underside surface 51 of the substrate. The ejected droplet may be retained on the substrate surface by solidifying thereon after contact; in such an embodiment, it is necessary to maintain the substrate at a low temperature, i.e., a temperature that results in droplet solidification after contact. Alternatively, or in addition, a molecular moiety within the droplet attaches to the substrate surface after contact, through adsorption, physical immobilization, or covalent binding.

Figure 1B:
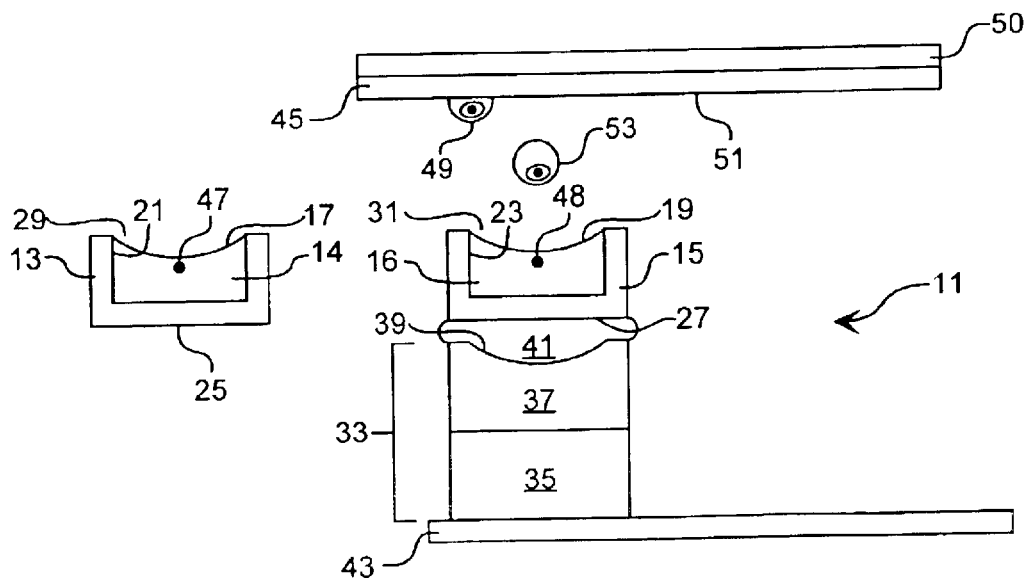
Figure 5B:
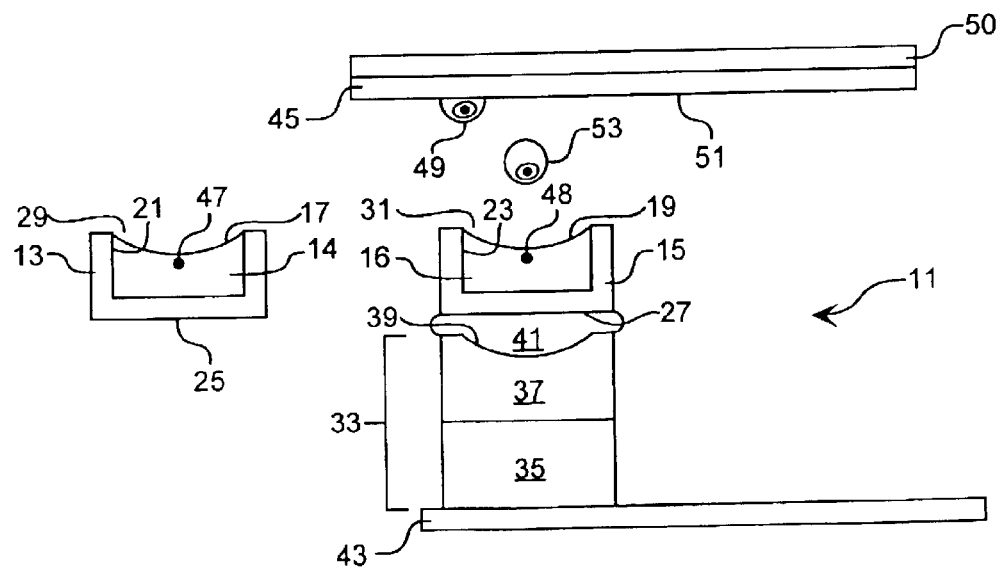
Figure 5C:
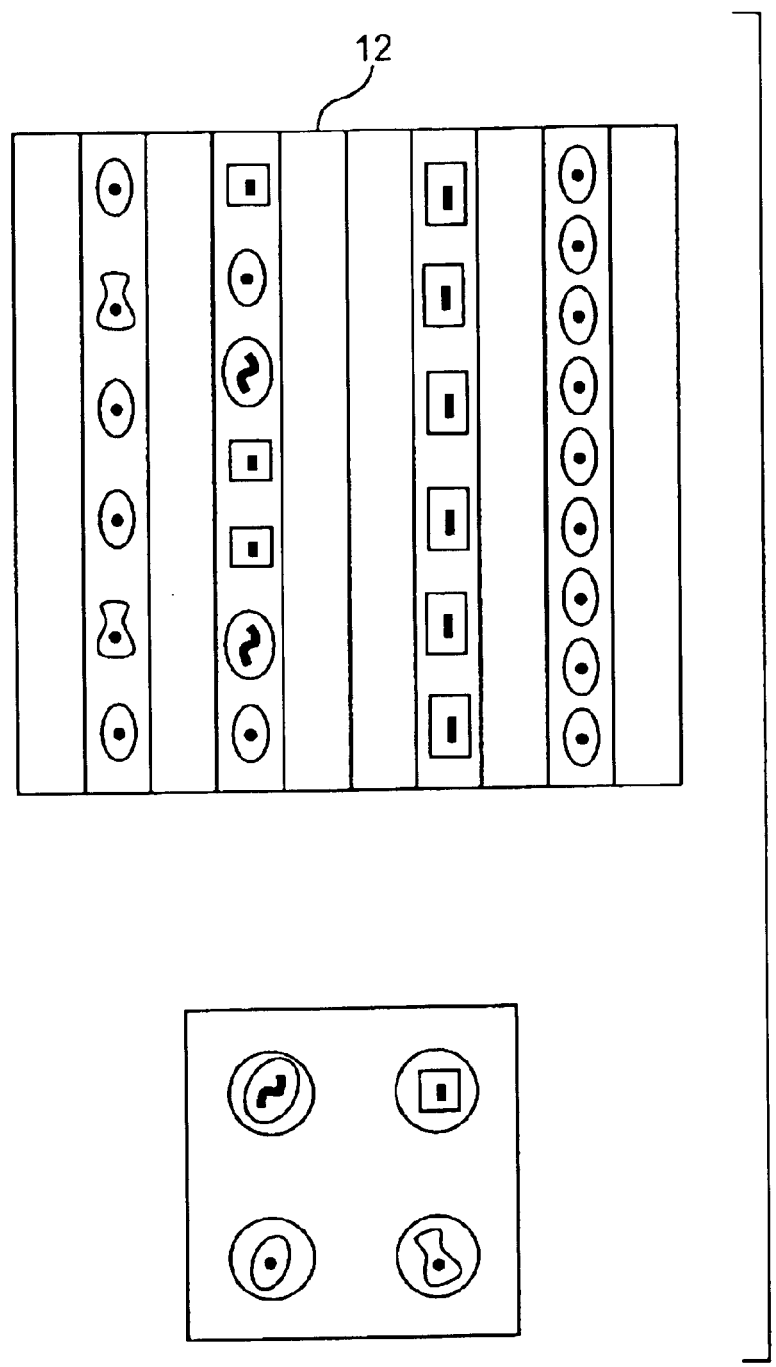

Next, as shown in FIGS. 1B and 5B, a substrate positioning means 50 repositions the substrate 45 over reservoir 15 in order to receive a droplet therefrom at a second designated site. FIGS. 1B and 5B also show that the ejector 33 has been repositioned by the ejector positioning means 43 below reservoir 15 and in acoustically coupled relationship thereto by virtue of acoustic coupling medium 41. Once properly aligned as shown in FIGS. 1B and 5B, the acoustic radiation generator 35 of ejector 33 is activated to produce acoustic radiation that is then directed by focusing means 37 to a focal point within fluid 16 near the fluid surface 19, thereby ejecting droplet 53 onto the substrate. It should be evident that such operation is illustrative of how the employed device may be used to eject a plurality of single cells contained in fluid droplets from reservoirs in order to form a pattern, e.g., an array, of cells on the substrate surface 51. It should be similarly evident that the device may be adapted to eject a plurality of individual cells contained in ejected fluid droplets from one or more reservoirs onto the same site of the substrate surface.

Figure 2A:
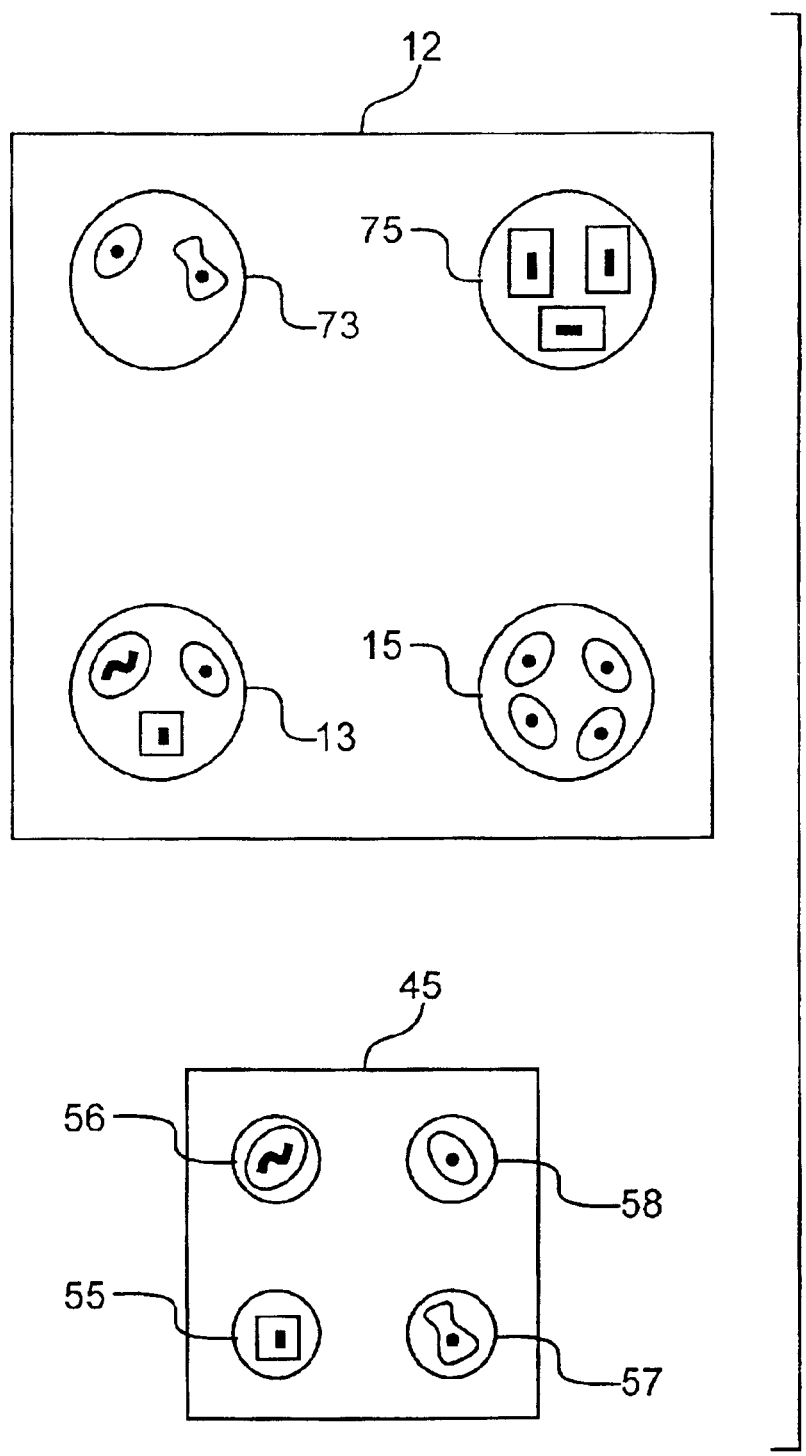
FIGS. 2A, 2B, and 2C, collectively referred to as FIG. 2, illustrate in schematic view a variation of the inventive embodiment of FIG. 1 wherein the cell containers or reservoirs comprise individual wells in a reservoir well plate, and the substrate comprises a smaller well plate with a corresponding number of wells.
Figure 2B:
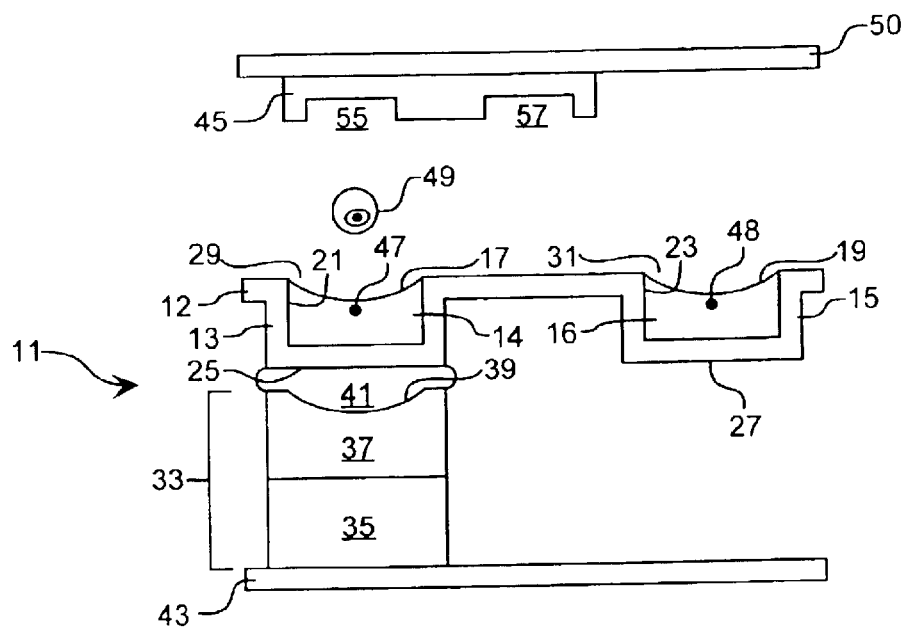

In another embodiment, the device is constructed so as to allow transfer of cells contained in fluid droplets between well plates, in which case the substrate comprises a substrate well plate, and the fluid suspended-cell-containing reservoirs are individual wells in a reservoir well plate. FIG. 2 illustrates such a device, wherein four individual wells 13, 15, 73, and 75 in reservoir well plate 12, serve as fluid reservoirs for containing a plurality of a specific type of cell, or a mixture of different cell types, suspended in a fluid for ejection of droplets containing a single cell, and the substrate comprises a smaller well plate 45 of four individual wells indicated at 55, 56, 57, and 58. FIG. 2A illustrates the cell container or reservoir well plate and the substrate well plate in top plane view. As shown, each of the well plates contains four wells arranged in a two-by-two array. FIG. 2B illustrates the employed device wherein the cell container or reservoir well plate and the substrate well plate are shown in cross-sectional view along wells 13, 15 and 55, 57, respectively. As in FIGS. 1 and 5, reservoir wells 13 and 15 respectively contain cells suspended in carrier fluids 14 and 16 having carrier fluid surfaces respectively indicated at 17 and 19. The materials and design of the wells of the cell container or reservoir well plate are similar to those of the containers illustrated in FIGS. 1 and 5. For example, the cell containers or reservoirs shown in FIG. 2B (wells) and in FIG. 5B (channels) are of substantially identical construction so as to be substantially acoustically indistinguishable. In these embodiments, the bases of the cell reservoirs are of a material (e.g., a material having appropriate acoustic impedance) and thickness so as to allow efficient transmission of acoustic radiation therethrough into the contained carrier fluid.

The device of FIGS. 2 and 5 also includes an acoustic ejector 33 having a construction similar to that of the ejector illustrated in FIG. 1, comprising an acoustic generating means 35 and a focusing means 37. FIG. 2B shows the ejector acoustically coupled to a reservoir well through indirect contact; that is, an acoustic coupling medium 41 is placed between the ejector 33 and the reservoir well plate 12, i.e., between the curved surface 39 of the acoustic focusing means 37 and the base 25 of the first cell container or reservoir (well or channel) 13. As shown, the first cell container or reservoir (well or channel) 13 is acoustically coupled to the acoustic focusing means 37 such that acoustic radiation generated in a generally upward direction is directed by the focusing means 37 into the acoustic coupling medium 41, which then transmits the acoustic radiation into the cell container or reservoir (well or channel) 13.

In operation, each of the cell containers or reservoirs (well or channel) is preferably filled with a carrier fluid having a different type of cell or mixture of cells suspended within the carrier fluid. As shown, reservoir wells 13 and 15 of the device are each filled with a carrier fluid having a first cell mixture 14 and a carrier fluid having a second cell mixture 16, as in FIG. 1, to form fluid surfaces 17 and 19, respectively. FIGS. 1 and 5 show that the ejector 33 is positioned below reservoir well 13 by an ejector positioning means 43 in order to achieve acoustic coupling therewith through acoustic coupling medium 41.

For the ejection of individual cells into well plates from cell containers, FIG. 2A shows that the first substrate well 55 of substrate well plate 45 is positioned above the first reservoir well 13 in order to receive a droplet ejected from the first cell container or reservoir (well or channel).

Figure 5D:
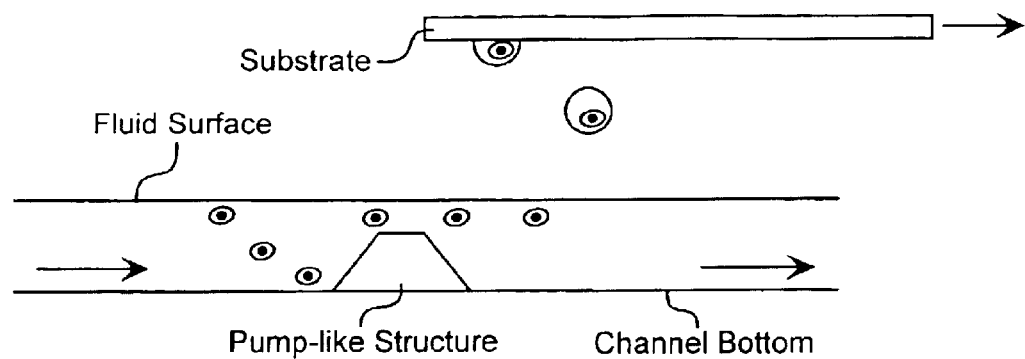
FIG. 5D illustrates a cross-section of a channel showing an upward protrusion of the channel floor to direct cells sufficiently close to the fluid surface for ejection.
Figure 5E:
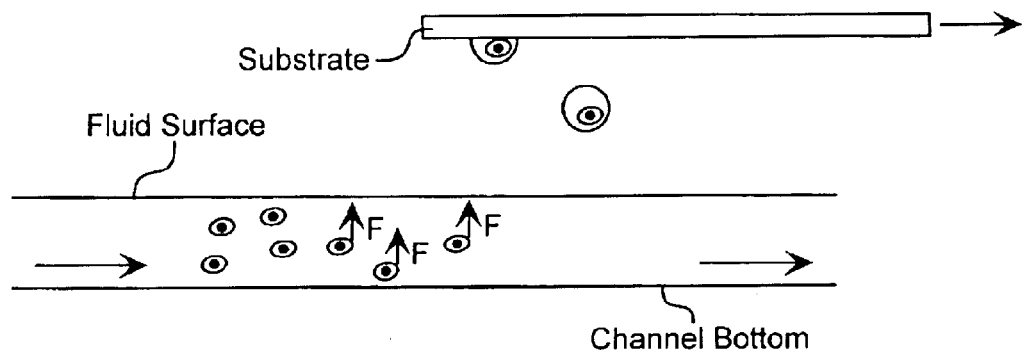
FIG. 5E illustrates a cross-section of a channel showing the use of focused energy, such as acoustic energy, to direct cells sufficiently close to the fluid surface for ejection.

Once the ejector, the cell container or reservoir (well or channel), and the substrate are in proper alignment, the acoustic radiation generator is activated to produce an acoustic wave that is focused by the focusing means to direct the acoustic wave to a focal point 47 near fluid surface 17, with the amount of energy being insufficient to eject fluid. This first emission of focused acoustic energy permits sonic detection of the presence of a cell sufficiently close to the surface for ejection by virtue of reflection of acoustic energy, said reflection due to a difference in acoustic impedance between the cell and the carrier fluid. After a cell is detected and localized, other properties may be measured before the decision to eject is made. Also, if no cell is sufficiently close to the surface for ejection, the acoustic energy may be focused at progressively greater distances from the fluid surface until a cell is located and driven closer to the surface by focused acoustic energy. Alternatively, a uniform field may be used to move the cell closer to the surface. One such field is a photon field, which will exert a force based on cross sectional area and change in photon momentum, determined by the difference of refractive indices of the carrier medium and the cells. Another such field is an electric field, which exerts a force based on net surface charge. It will be appreciated that there are numerous ways of effecting a short mean cell distance from the fluid surface. For channels, especially microfabricated channels, mechanical means may be used to effect a sufficiently small distance from the fluid surface by placing a ramp-like structure across the channel, which decreases channel depth over the ramp to a depth on the order of the cell diameter, thereby only permitting cells to flow near the surface; cells are unlikely to jam at the ramp because the fluid velocity will be highest where the channel depth is lowest, as depicted in FIG. 5D. FIG. 5E depicts a microfluidic channel where a force acting on the cells moves them towards the surface.

Because microfluidic channels may be fabricated with small dimensions that reduce the volume in which a cell may be located, they are especially preferred for use with acoustic ejection, as locating a cell suitable for ejection is greatly simplified. For example, for a cell type or mixture of cell types having a relatively uniform size, for example a mean diameter of 10.0 μm, SD. 0.5 μm, the channel can be engineered to be about 12.0 μm wide and deep, creating a single file of cells at a mean distance of about 1.0 μm from the fluid surface (ejection volume $4/3\pi r^3$=0.52 pL). In such a case it is not necessary to provide a ramp or any other means to shorten the distance between the surface and the cell location. The cells can be ejected from the channel at a certain limited distance range along the fluid flow axis, reducing the area of fluid surface scanned. For example, a 50 μm aperture for ejecting cells can be provided in a closed capillary, or a limited distance along the flow axis of an open capillary may be used for ejection, a significant advantage being that the cells move past the ejector, reducing the area scanned for cells. Even when employing such methods to float cells in a macro-scale container such as a petri dish, significant amounts of time will be wasted scanning in the plane parallel to the fluid surface to locate a cell to eject. The advantages of employing microfluidic channels are only slightly diminished for a wider range of cell sizes; for example, red blood cells (RBC, mean diameter of 7 μm SD. 0.3 μm, biconcave disc, height 0.3 μm) mixed with the preceding cell type (mean diameter of 10.0 μm, SD. 0.5 μm). Although the RBCs can be a significant depth from the surface relative to the fluid ejection volume, and thus significant energy is required to eject a RBC, this situation can be overcome by the described methods of forcing cells toward the fluid surface. The advantage of limiting the lateral search to a width of about 12 μm, as opposed to the several cm width of a petri dish, is immediately apparent Once a cell sufficiently close to the surface is located and is determined to meet any other criteria for ejection, the acoustic radiation generator is activated to produce an acoustic wave that is focused by the focusing means to direct the acoustic wave to a focal point 47 near fluid surface 17, with the amount of energy being sufficient to eject a volume of fluid substantially corresponding to the volume of the cell to be ejected, so that any ejected volume does not contain more than one cell. The precise amount of energy required to eject only the required volume and no more can be initially calibrated by slowly increasing the energy applied, from an amount insufficient to eject a cell desired for ejection until there is just enough energy applied to eject the cell the desired distance to the targeted substrate locale. After this initial calibration, approximately the same energy, with adjustment for any change in fluid level, may be applied to eject cells of substantially the same volume as the initial calibration cell. As a result, droplet 49, containing a single living cell, is ejected from fluid surface 17 into the first substrate well 55 of the substrate well plate 45. The cell-containing droplet is retained on the substrate well plate by surface tension.

Figure 2C:
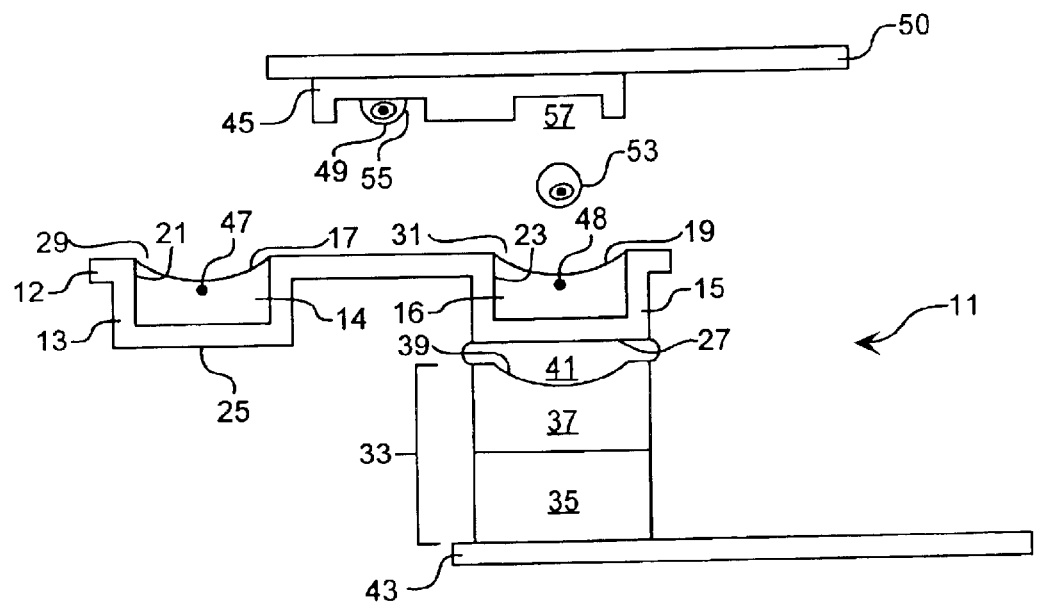

Then, as shown in FIG. 2C, the substrate well plate 45 is repositioned by a substrate positioning means 50 such that substrate well 57 is located directly over cell container or reservoir (well or channel) 15 in order to receive a cell-containing droplet therefrom. FIG. 2C also shows that the ejector 33 has been repositioned by the ejector positioning means below cell container well 15 to acoustically couple the ejector and the container through acoustic coupling medium 41. Since the substrate well plate and the reservoir well plate or channels on a planar substrate are of different sizes, there is only correspondence, not identity, between the movement of the ejector positioning means and the movement of the substrate well plate. Once properly aligned, as shown in FIG. 2C, the acoustic radiation generator 35 of ejector 33 is activated to produce an acoustic wave that is then directed by focusing means 37 to a focal point near the fluid surface 19; this wave is used to detect the presence of a cell that is sufficiently close to the carrier fluid surface to be ejected. After such a cell is detected, and any properties that are used as criteria for ejection are measured, the acoustic radiation generator 35 of ejector 33 is activated to produce an acoustic wave that is then directed by focusing means 37 to a focal point near the fluid surface 19 from which cell-containing droplet 53 is ejected onto the second well of the substrate well plate. It should be evident that such operation is illustrative of how the employed device may be used to transfer a plurality of single cells contained in appropriately sized droplets from one well plate to another of a different size. One of ordinary skill in the art will recognize that this type of transfer may be carried out even when the cells, the carrier fluid, and both the ejector and substrate are in continuous motion. It should be further evident that a variety of combinations of reservoirs, well plates, and/or substrates may be used in the employed device for transferring droplets that contain single cells. It should be still further evident that any reservoir may be filled with a fluid carrier, or with a fluid carrier containing suspended cells, through acoustic ejection of cell-free or cell-containing fluid droplets, respectively, prior to deploying the reservoir for further transfer of fluid droplets containing cells, e.g., for cell array deposition.

As discussed above, either individual (e.g., removable) reservoirs (well or channel) or plates (well or channel) may be used to contain cell suspensions in carrier fluids for ejection; the reservoirs or the wells of the well plate are preferably substantially acoustically indistinguishable from one another. Also, unless it is intended that the ejector be submerged in the fluid, the reservoirs or well plates must have acoustic transmission properties sufficient to allow acoustic radiation from the ejector to be conveyed to the surfaces of the fluids to be ejected. Typically, this involves providing reservoir or well bases that are sufficiently thin relative to the acoustic impedance of the material from which they are made, to allow acoustic radiation to travel therethrough without unacceptable dissipation. In addition, the material used in the construction of reservoirs must be compatible with the contained carrier fluids, and be non-toxic to the suspended cells.

Thus, as the reservoirs or wells are intended to contain live cells suspended in an aqueous carrier, any fluid materials that dissolve or swell in water, or that release compounds toxic to living cells into the aqueous carrier, would be unsuitable. For water-based fluids, a number of materials are suitable for the construction of reservoirs; these include, but are not limited to, ceramics such as silicon oxide and aluminum oxide, metals such as stainless steel and platinum, and polymers such as polyester and polytetrafluoroethylene. These materials may be prepared so that substances toxic to cells do not leach into the carrier fluid in sufficient amounts to render the carrier fluid toxic to the cells. Many well plates suitable for use with the employed device are commercially available and may contain, for example, 96, 384, or 1536 wells per well plate. Manufactures of suitable well plates for use in the employed device include Corning Inc. (Corning, N.Y.) and Greiner America, Inc. (Lake Mary, Fla.). The availability of such commercially available well plates does not, however, preclude the manufacture and use of custom-made well plates containing at least about 10,000 wells, or as many as 100,000 wells or more. For array forming applications, it is expected that about 100,000 to about 4,000,000 reservoirs may be employed. In addition, to reduce the amount of movement needed to align the ejector with each reservoir or reservoir well, it is preferable that the center of each reservoir be located not more than about 1 centimeter, preferably not more than about 1 millimeter, and optimally not more than about 0.5 millimeter, from any other reservoir center.

Generally, the device may be adapted to eject fluids of virtually any type and amount desired. Ejected fluid may be aqueous and/or nonaqueous, but only aqueous fluids are compatible with the transfer of living cells. Examples of aqueous fluids include water per se, water-solvated ionic and non-ionic solutions, suspensions or slurries of solids, gels, and aqueous liquids containing discrete cells. Because of the precision that is possible using the inventive technology, the device may be used to eject droplets from a reservoir adapted to contain no more than about 100 nanoliters of fluid, preferably no more than about 10 nanoliters of fluid. In certain cases, the ejector may be adapted to eject a droplet from a reservoir adapted to contain about 1 to about 100 nanoliters of fluid. This is particularly useful when the fluid to be ejected contains rare or expensive biomolecules or cells, wherein it may be desirable to eject droplets having a volume of about up to 1 picoliter.

From the above descriptions, it is evident that various components of the device may require individual control or synchronization to form an array of cells on a substrate. For example, the ejector positioning means may be adapted to eject droplets from each cell container or reservoir in a predetermined sequence associated with an array to be prepared on a substrate surface. Similarly, the substrate positioning means for positioning the substrate surface with respect to the ejector may be adapted to position the substrate surface to receive droplets in a pattern or array thereon. Either or both positioning means, i.e., the ejector positioning means and the substrate positioning means, may be constructed from, e.g., levers, pulleys, gears, linear motors, a combination thereof, or other mechanical means known to one of ordinary skill in the art. It is preferable to ensure that there is a correspondence between the movement of the substrate, the movement of the ejector, and the activation of the ejector to ensure proper pattern formation.

Moreover, the device may include other components that enhance performance. For example, as alluded to above, the device may further comprise cooling means for lowering the temperature of the substrate surface to ensure, for example, that the ejected droplets adhere to the substrate and that the cells rapidly freeze to maintain their viability. The cooling means may be adapted to maintain the substrate surface at a temperature that allows fluid to partially, or preferably completely, freeze shortly after the cell-containing fluid droplet comes into contact with it. In the case of aqueous fluid droplets containing cells, the cooling means should have the capacity to maintain the substrate surface at no more than about 0° C., preferably much colder. In addition, repeated application of acoustic energy to a reservoir of fluid may result in heating of the fluid. Heating can, of course, result in unwanted effects on living cells. Thus, the device may further comprise means for maintaining fluid in the cell containers or reservoirs at a constant temperature. Design and construction of such temperature-maintaining means are known to one of ordinary skill in the art and may comprise, e.g., components such a heating element, a cooling element, or a combination thereof. For biomolecular and live cell deposition applications, it is generally desired that the fluid containing the biomolecule or cells be kept at a constant temperature, with deviations of no more than about 1° C. or 2° C. In addition, for live cells, it is preferred that the fluid be kept at a temperature that does not exceed about 1° C. above the normal temperature from which the cell is derived in the case of warm blooded organisms, and at about 16° C. for all other organisms, whether prokaryotic or eukaryotic, except for specific cell types known to have poor viability unless chilled. Cells that require chilling for viability will be appreciated by those of ordinary skill in the art of culturing and maintaining cells to require a saline carrier fluid of appropriate osmolality (slightly hyperosmotic) at about 4° C. Thus, for example, when the biomolecule-containing fluid is aqueous, it may be optimal to keep the fluid at about 4° C. during ejection.

The invention may involve modification of a substrate surface prior to receiving acoustically ejected cell-containing fluid droplets. Surface modification may involve functionalization or defunctionalization, smoothing or roughening, coating, degradation, passivation, or other alterations of the surface's chemical composition or physical properties. In one embodiment, the invention requires functionalization with a moiety cognate to an externally displayed marker moiety, but other surface modifications described may affect the success of the inventive method in a specific context One such surface modification method involves altering the wetting properties of the surface. Such a method can be used, for example, to facilitate confinement of a cell contained in a droplet ejected onto the surface within a designated area, or to enhance the surface attachment of molecular moieties used for functionalizing the substrate or a specific substrate locale (such as patterned biotinylation accomplished by acoustic ejection of a biotinylating solution). A preferred method for altering the wetting properties of the substrate surface involves deposition of droplets of a suitable surface modification fluid at each designated site of the substrate surface prior to acoustic ejection of fluids to form an array thereon. In this way, the "spread" of the acoustically ejected droplets and contained cells may be optimized, and consistency in spot size (i.e., diameter, height, and overall shape) ensured. One way to implement the method involves acoustically coupling the ejector to a modifier reservoir containing a surface modification fluid and then activating the ejector, as described in detail above, to produce and eject a droplet of surface modification fluid toward a designated site on the substrate surface. The method is repeated as desired to deposit surface modification fluid at additional designated sites. Similarly, by the methods of copending applications U.S. Ser. No 09/964,193 ("Focused Acoustic Energy in the Preparation and Screening of Combinatorial Libraries," inventors Mutz and Ellson), filed Sep. 25, 2001, and U.S. Ser. No. 09/963,173 ("Focused Acoustic Energy in the Preparation of Peptide Arrays," inventors Mutz and Ellson), also filed Sep. 25, 2001, both of which are assigned to Picoliter, Inc. (Mountain View, Calif.)) or by other methods of generating arrays of biomolecules attached or linked to a substrate surface, cognate moieties that specifically bind to marker moieties displayed on the surface of transformed or untransformed cells may be patterned on the substrate surface. Alternatively, a single cognate moiety such as biotin can be linked to the substrate surface either uniformly, or in a pattern (such as a pattern of biotinylated areas surrounded by non-biotinylated areas). The cells to be patterned can be transformed to display streptavidin on their surface.

FIG. 3 schematically illustrates in simplified cross-sectional view a specific embodiment of the aforementioned method, in which a dimer is synthesized on a substrate using a device similar to that illustrated in FIG. 1, but including a modifier reservoir 59 containing a surface modification fluid 60 having a fluid surface 61. FIG. 3A illustrates the ejection of a droplet 63 of surface modification fluid 60 selected to alter the wetting properties of a designated site on surface 51 of the substrate 45 where the dimer is to be synthesized. The ejector 33 is positioned by the ejector positioning means 43 below the modifier reservoir 59 in order to achieve acoustic coupling therewith through an acoustic coupling medium 41. Substrate 45 is positioned above the modifier reservoir 19 at a location that enables acoustic deposition of a droplet of surface modification fluid 60 at a designated site. Once the ejector 33, the modifier reservoir 59, and the substrate 45 are in proper alignment, the acoustic radiation generator 35 is activated to produce acoustic radiation that is directed by the focusing means 37 in a manner that enables ejection of droplet 63 of the surface modification fluid 60 from the fluid surface 61 onto a designated site on the underside surface 51 of the substrate. Once the droplet 63 contacts the substrate surface 51, the droplet modifies an area of the substrate surface to produce an increase or decrease in the surface energy of the area with respect to the deposited fluids.

Figure 3A:
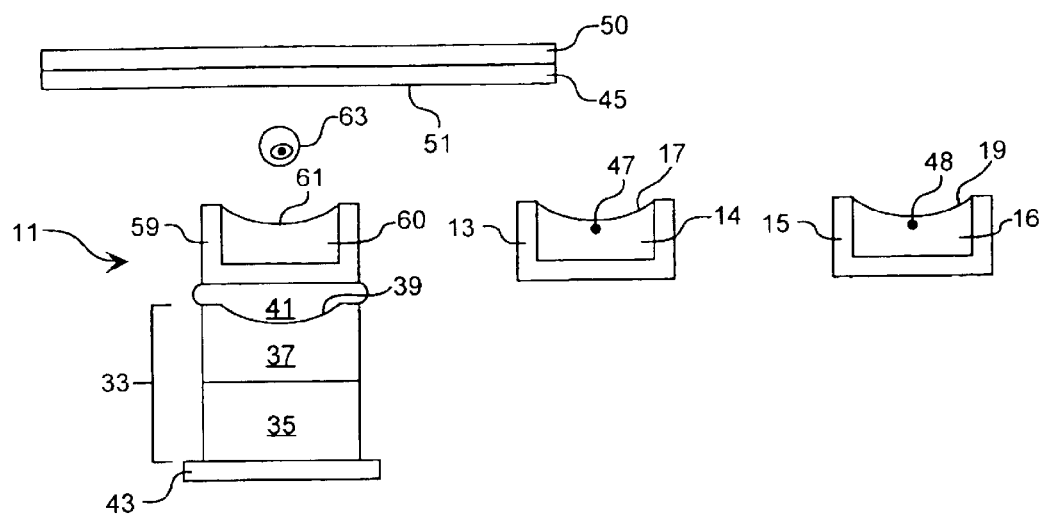
FIGS. 3A, 3B, 3C, and 3D, collectively referred to as FIG. 3, schematically illustrate in simplified cross-sectional view an embodiment of the inventive method in which cells having an externally displayed marker moiety are ejected onto a substrate using the device of FIG. 1.
Figure 3B:
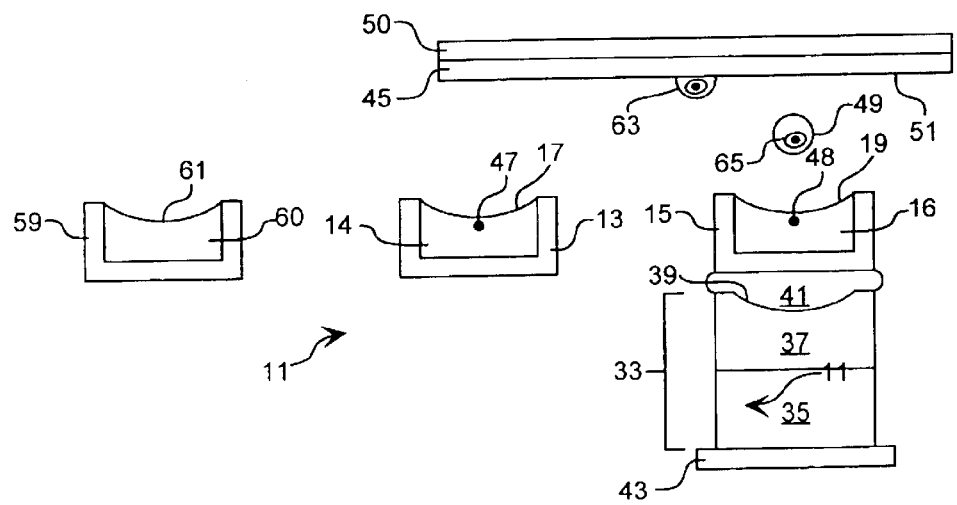

Next, as shown in FIG. 3B, the substrate 45 is repositioned by the substrate positioning means 50 such that the region of the substrate surface modified by droplet 63 is located directly over reservoir 13. FIG. 3B also shows that the ejector 33 is positioned by the ejector positioning means below reservoir 13 to acoustically couple the ejector and the reservoir through the acoustic coupling medium 41. Once properly aligned, the ejector 33 is again activated so as to eject droplet 49 onto the substrate. Droplet 49 contains a single cell 65, preferably displaying a marker moiety on its external cell membrane that is specifically bound by a cognate moiety linked to the surface to effect specific attachment to the surface. The marker moiety may occur in an untransformed cell or may be the result of transformation or genetic manipulation, and may optionally signify transformation such that a gene other than the marker is expressed, e.g. the marker is a reporter of transformation by another gene.

Figure 3C:
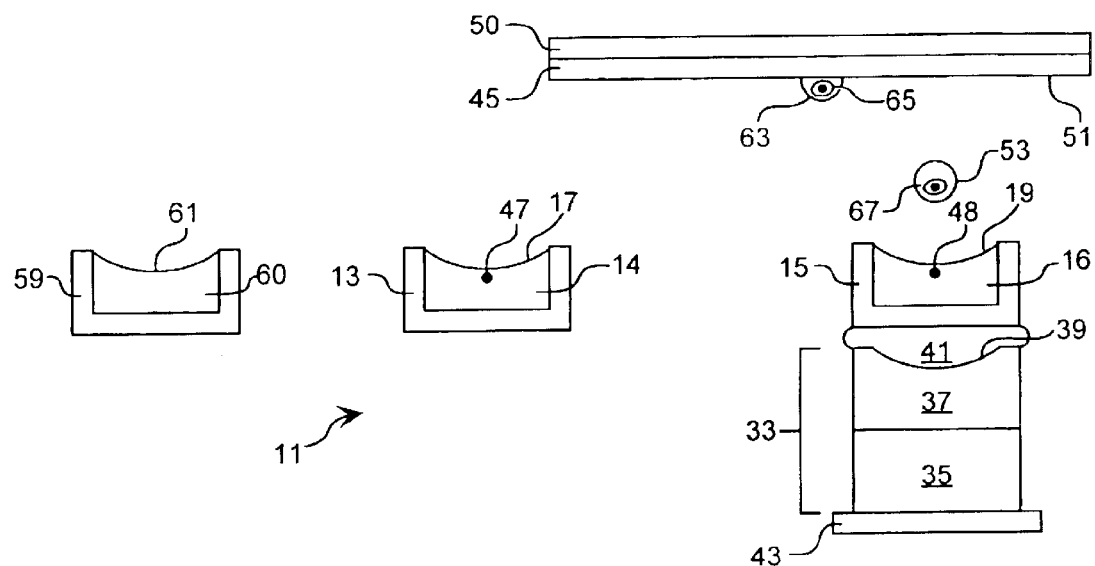
Figure 3D:
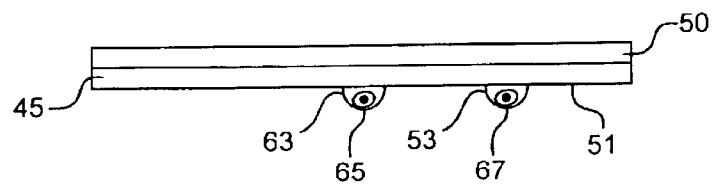
Figure 4A:
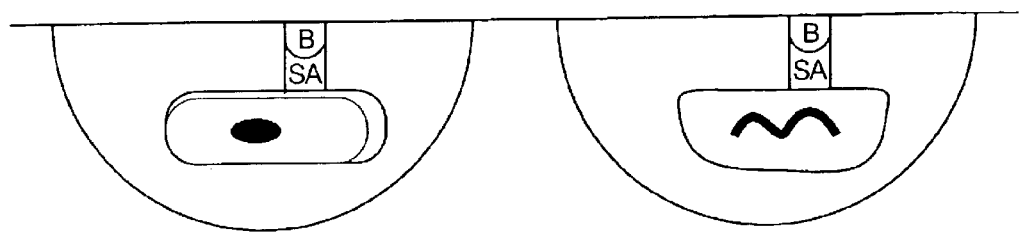
FIGS. 4A and 4B, collectively referred to as FIG. 4, depict arrayed cells contained in droplets deposited by acoustic ejection using the device of FIG. 1.
Figure 4B:
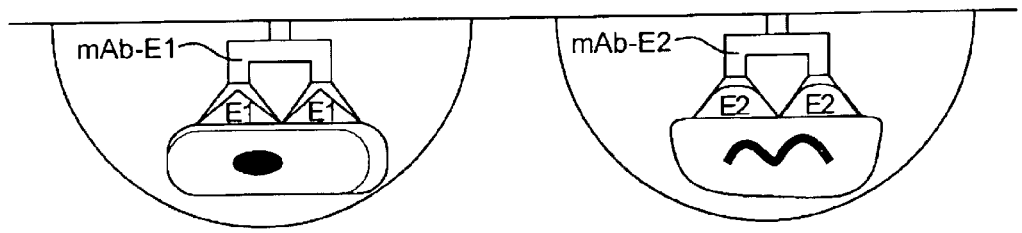

As shown in FIG. 3C, the substrate 45 is again repositioned by the substrate positioning means 50 such that a different site than the site where the first single cell 65 is attached is located directly over reservoir 15 in order to receive a cell contained in another droplet. FIG. 3B also shows that the ejector 33 is positioned by the ejector positioning means below reservoir 15 to acoustically couple the ejector and the reservoir through acoustic coupling medium 41. Once properly aligned, the ejector 33 is again activated so that droplet 53 is ejected onto the substrate. Droplet 53 contains a second single cell.

Cognate moieties are commonly ligands, including oligonucleotides and peptides. Marker moieties are likely to be peptides or peptidoglycans. The chemistry employed in synthesizing substrate-bound oligonucleotides can be adapted to acoustic fluid droplet ejection; see co-pending U.S. Ser. No. 09/964,212 ("Acoustic Ejection of Fluids from a Plurality of Reservoirs"), inventors Ellson, Foote, and Mutz, referenced supra. These methods may be used to create arrays of oligonucleotides on a substrate surface for use with the instant invention. Such adaptation will generally involve now-conventional techniques known to those skilled in the art of nucleic acid chemistry and/or described in the pertinent literature and texts. See, for example, *DNA Microarrays: A Practical Approach*, M. Schena, Ed. (Oxford University Press, 1999). That is, the individual coupling reactions are conducted under standard conditions used for the synthesis of oligonucleotides and conventionally employed with automated oligonucleotide synthesizers. Such methodology is described, for example, in D. M. Matteuci et al. (1980) *Tet. Lett.* 521:719, U.S. Pat. No. 4,500,707 to Caruthers et al., and U.S. Pat. Nos. 5,436,327 and 5,700,637 to Southern et al. Focused acoustic energy may also be adapted for in situ combinatorial oligonucleotide, oligopeptide, and oligosaccharide syntheses; these syntheses may be used to produce combinatorial arrays for use with the instant invention. See co-pending U.S. Ser. No. 09/964,193 ("Focused Acoustic Energy in the Preparation and Screening of Combinatorial Libraries," inventors Mutz and Ellson), referenced supra.

Alternatively, an oligomer may be synthesized prior to attachment to the substrate surface and then "spotted" onto a particular locus on the surface using the methodology of the invention. Again, the oligomer may be an oligonucleotide, an oligopeptide, an oligosaccharide, or any other biomolecular (or nonbiomolecular) oligomer moiety. Preparation of substrate-bound peptidic molecules, e.g., those used in the formation of peptide arrays and protein arrays, is described in co-pending patent application U.S. Ser. No. 09/963,173 ("Focused Acoustic Energy in the Preparation of Peptide Arrays," inventors Mutz and Ellson), filed on Sep. 25, 2001 and assigned to Picoliter, Inc. (Mountain View, Calif.) or by other methods of generating arrays. Preparation of substrate-bound oligonucleotides, particularly arrays of oligonucleotides wherein at least one of the oligonucleotides contains partially nonhybridizing segments, is described in co-pending patent application U.S. Ser. No. 09/962,731 ("Arrays of Partially Nonhybridizing Oligonucleotides and Preparation Thereof Using Focused Acoustic Energy"), inventor Ellson, also filed on Sep. 24, 2001 and assigned to Picoliter, Inc. (Mountain View, Calif.)

These acoustic ejection methods for use with the instant invention enable preparation of molecular arrays, particularly biomolecular arrays, having densities substantially higher than those possible using current array preparation techniques, such as photolithographic processes, piezoelectric techniques (e.g., using inkjet printing technology), and microspotting. The array densities that may be achieved using the devices and methods of the invention are at least about 1,000,000 biomolecules per square centimeter of substrate surface, preferably at least about 1,500,000 per square centimeter of substrate surface. The biomolecular moieties may be, e.g., peptidic molecules and/or oligonucleotides. Often such densities are not necessary for creating sites containing individual cells, which are separated by a distance from other cells. But adaptation of such methods, for example, to functionalize a discrete portion of a site surface with a cognate moiety that specifically binds a marker moiety, may be useful for localizing the cells within the site, or for deliberately arraying the cells in close proximity to each other. For example, a lymphocyte array, consisting of small (8 $\mu$m), medium (12 $\mu$m), or large (14 $\mu$m) cells, may be created by functionalizing a 10 $\mu$m diameter spot in the center of each 100 $\mu$m×100 $\mu$m site with the appropriate cognate moiety to specifically bind the spotted cell. This arrangement will ensure sufficient cell separation to allow, for example, testing or screening of individual cells by acoustically deposited reagent-containing fluid droplets of sufficient volume to expose or treat the cell, without exposing cells at adjacent sites to the fluid. Thus, for example, combinatorial screening of cells is permitted.

It should be evident, then, that many variations of the invention are possible. For example, each of the ejected cell-containing droplets may be deposited as an isolated and "final" feature. Alternatively, or in addition, a plurality of ejected droplets, each containing one or a plurality of cells, may be deposited at the same location on a substrate surface in order to synthesize a cell array where each site contains multiple cells of ascertainable number. This method may be used to pattern cells for other purposes, such as to engineer a tissue based on the replication of a specific histologic architecture. For cell array and patterning fabrication techniques that involve attachment of cells to a substrate surface, it is expected that washing steps may be used between droplet ejection steps. Such washing steps may involve, e.g., submerging the entire substrate surface on which cells have been deposited in a washing fluid.

The invention enables ejection of droplets at a rate of at least about 1,000,000 droplets per minute from the same reservoir, and at a rate of at least about 100,000 drops per minute from different reservoirs. In addition, current positioning technology allows for the ejector positioning means to move from one cell container or reservoir to another quickly and in a controlled manner, thereby allowing fast and controlled ejection of different fluids. That is, current commercially available technology allows the ejector to be moved from one reservoir to another, with repeatable and controlled acoustic coupling at each reservoir, in less than about 0.1 second for high performance positioning means and in less than about 1 second for ordinary positioning means. A custom designed system will allow the ejector to be moved from one reservoir to another with repeatable and controlled acoustic coupling in less than about 0.001 second.

In order to provide a custom designed system, it is important to keep in mind that there are two basic kinds of motion: pulse and continuous. Pulse motion involves the discrete steps of moving an ejector into position, emitting acoustic energy, and moving the ejector to the next position; again, using a high performance positioning means with such a method allows repeatable and controlled acoustic coupling at each reservoir in less than 0.1 second. A continuous motion design, on the other hand, moves the ejector and the reservoirs continuously, although not at the same speed, and provides for ejection while these movements are occurring. Since the pulse width is very short, this type of process enables reservoir transitions to occur at a rate of more than 10 Hz, and even more than 1000 Hz.

In order to ensure the accuracy of fluid ejection, it is important to determine the location and the orientation of the fluid surface from which a droplet is to be ejected with respect to the ejector. Otherwise, ejected droplets may be improperly sized or travel in an improper trajectory. Thus, another embodiment of the invention relates to a method for determining the height of a fluid surface and the proximity of a cell in a reservoir between ejection events. The method involves acoustically coupling a fluid-containing reservoir to an acoustic radiation generator, and then activating the generator to produce a detection acoustic wave that travels to the fluid surface and is reflected therefrom as a reflected acoustic wave. Parameters of the reflected acoustic radiation are then analyzed in order to assess the spatial relationship between the acoustic radiation generator and the fluid surface. Such an analysis will involve the determination of the distance between the acoustic radiation generator and the fluid surface and/or the orientation of the fluid surface in relationship to the acoustic radiation generator.

More particularly, the acoustic radiation generator may be activated so as to generate low energy acoustic radiation that is insufficiently energetic to eject a droplet from the fluid surface. This is typically done by using an extremely short pulse (on the order of tens of nanoseconds) relative to that normally required for droplet ejection (on the order of microseconds). By determining the time it takes for the acoustic radiation to be reflected by the fluid surface back to the acoustic radiation generator, and then correlating that time with the speed of sound in the fluid, the distance—and thus the fluid height—may be calculated. The distance of a cell in the fluid from the fluid surface can be determined in the same manner. Of course, care must be taken in order to ensure that acoustic radiation reflected by the interface between the reservoir base and the fluid is discounted. It will be appreciated by those of ordinary skill in the art that such a method employs conventional or modified sonar techniques.

Once the analysis has been performed, an ejection acoustic wave having a focal point close to a cell center near the fluid surface is generated, in order to eject at least one droplet of the fluid, wherein the optimum intensity and directionality of the ejection acoustic wave is determined using the aforementioned analysis, optionally in combination with additional data. The "optimum" intensity and directionality are generally selected to produce droplets of consistent size and velocity. For example, the desired intensity and directionality of the ejection acoustic wave may be determined by using not only the spatial relationship assessed as above, but also: geometric data associated with the reservoir, fluid property data associated with the fluid to be ejected, cell dimensions and consequent cell volume, and/or historical cell-containing droplet ejection data associated with the ejection sequence. In addition, the data may show the need to reposition the acoustic radiation generator with respect to the fluid surface, in order to ensure that the focal point of the ejection acoustic wave is near the fluid surface, where desired. For example, if analysis reveals that the acoustic radiation generator is positioned such that the ejection acoustic wave cannot be focused near the fluid surface, the acoustic radiation generator is repositioned using vertical, horizontal, and/or rotational movement to allow appropriate focusing of the ejection acoustic wave.

Because one aspect of the invention is ejection of a single cell, the selective nature of the invention will be immediately appreciated. Using simple ejection, cells of sufficiently different size can be separated, starting with ejection of the smallest cells. The device can thus be employed as a type of cell sorter, in addition to its use for making arrays. For example, because monocytes (diameter 20 $\mu$m) are much larger than both small (diameter 8 $\mu$m) and medium and large lymphocytes (diameter 12–14 $\mu$m) (corresponding to a cellular volume for monocytes about 3 times greater than that of large lymphocytes, and about 16 times greater than that of small lymphocytes), a mixture of these cells may be selectively ejected for arraying or sorting. The minimum acoustic energy level adequate to eject small lymphocytes will be insufficient to eject large lymphocytes and monocytes.

Once all the small lymphocytes have been ejected, the large lymphocytes may be ejected using a minimum acoustic energy level adequate to eject large lymphocytes (which will be adequate for ejecting medium lymphocytes), with little danger of ejecting the much larger and heavier monocytes. Surface functionalization with cognate moieties to marker moieties displayed externally on a cell exterior offers another level of selectivity, albeit requiring ejection onto a surface. Finally, as the invention provides for acoustic location of a cell to determine whether it is close enough to the surface to be ejected, various properties may be measured and used as additional criteria for ejection. One of skill in the art of cell sorting will appreciate that such ejection with additional criteria can be adapted to traditional cell sorting applications, by ejection in a trajectory appropriate to transfer the ejected cell to another fluidic container, or by spotting onto a substrate and subsequently washing the desired cells into a container.

The ability to measure a property as an ejection criterion, in addition to permitting the invention to be used for cell sorting, permits the sorting of non-living solids, gels, and fluid regions discrete from the carrier fluid. It will be readily appreciated that the ejection of, for example, beads used for solid phase combinatorial synthesis and bearing some marker or property identifying the combinatorial sequence, may be separated by the method of the invention.

It is to be understood that while the invention has been described in conjunction with the preferred specific embodiments thereof, the foregoing description is intended to illustrate and not limit the scope of the invention. Other aspects, advantages and modifications will be apparent to those skilled in the art to which the invention pertains.

All patents, patent applications, journal articles and other references cited herein are incorporated by reference in their entireties.

The following examples are put forth so as to provide those of ordinary skill in the art with a complete disclosure and description of how to implement the invention, and are not intended to limit the scope of what the inventors regard as their invention.

EXAMPLE 1
Acoustic Ejection of Monocytes onto a Substrate to form an Array

Rabbit polyclonal-Ab against human MHC (displayed on all cells) is generated and a single clone is selected that binds an MHC epitope common to all humans rather than to the epitopes specific to individuals. A substrate is functionalized with the mAb by routine methods. Monocrystalline Si is chosen as the substrate because of the plethora of known methods for functionalizing Si. A channel 25 $\mu$m wide, 25 $\mu$m deep, and about 3 cm long, open on top for the last 0.5 cm, is utilized to economize on time spent searching for cells to eject. The channel is fabricated of an HF-etched glass plate heat fused to a cover glass plate by routine microfabrication techniques.

The channel is fluidically connected by routine methods to a fluid column to which the cell suspension is added. The dimensions of the column allow 5 mL of fluid carrier and cells to be added, so that a sufficient column pressure exists to initiate fluid flow through the channel to allow fluid to reach the open top area in a sufficiently short time. The top of the column is then connected to a pressure regulator that allows the gas pressure above the carrier fluid in the column to be regulated, to permit fine adjustment, termination, and reinitiation of the carrier fluid flow through the channel.

The carrier fluid may be a physiologic saline or other electrolyte solution having an osmolality about equivalent to that of blood serum. The monocytes are spotted onto a substrate maintained at about 38° C. The substrate employed is planar, and a density of 10,000 sites/cm$^2$ is chosen, with each site occupied by a single cell. Circulating monocytes from 10 different individuals are obtained and purified by routine methods.

The monocytes of each individual are attached to the array by acoustic ejection of a droplet having a volume of about 4.2 pL. Specifically, every tenth site of each row is spotted with monocytes from one individual, and the deposition of that individual's cells is staggered in subsequent rows to create increased separation between cells from an individual. Separation of an individual's cells is preferable because it provides an internal control against variations in conditions between different substrate areas. The monocytes from the remaining individuals are similarly spotted onto the array sites in acoustically ejected droplets. Ten duplicate arrays are made.

Because monocytes are attracted by chemotaxis into inflamed tissues, where they are transformed into macrophages under the influence of immune mediators, the arrays are studied by immersing them in various physiologic solutions containing one or more inflammatory mediators, such as histamine, interleukins (ILs), granulocyte macrophage colony stimulating factor (GM-CSF), leukotrienes, and other inflammatory mediators known in the art. They are also studied by exposing them to conditions that might affect inflammation, such as heat and known anti-inflammatory agents, including steroids, non-steroidal anti-inflammatory drugs, and random substances or those suspected to affect the activation of macrophages. It will be readily appreciated that certain mediators and combinations thereof will have pro- or anti-inflammatory effects, and that there will be differences between individuals and to a lesser extent between individual cells. Because the monocytes are attached by the mAb/MHC specific attachment, the array will not be disrupted by immersion.

The transformation of the monocytes into macrophages and of macrophages back to monocytes may be observed by light microscopy without affecting cell viability. Other known methods include EM (electron microscopy) and XPS (X-ray photoelectron spectroscopy) of individual cells. Because immune cells, especially activated macrophages, are able to activate immune cells by release of immune mediators and chemotactic agents, the possibility exists that one individual's monocytes may be unresponsive to an immune mediator or condition, but responsive to the immune mediators released by another individual's macrophage that was responsive to the experimental condition. To control for the preceding, standard well plates are used as controls using the identical method, with multiple monocytes from the same individual in each well (for 96 well plates, 9 wells/individual, 110 cells each). A final control, using well plates without the mAb/MHC attachment system, is also created by the method described, with surface tension sufficing to hold the ejected cell-containing droplets in place. It is readily appreciated that the 110 droplets deposited in each well plate are preferably deposited at different locations within the well to prevent droplets too big to be held in place by surface tension from being formed by multiple deposition.

EXAMPLE 2
Human Airway Epithelium (HAE) Cell Array for Studying Airway Immune and Inflammatory Response The method of the preceding example is adapted to HAE cells by providing a channel having appropriate dimensions (just larger than the HAE cells). Alternatively, the width of the channel is just wider than the cells; to permit faster loading, the depth is approximately three times the diameter of the cells and a ramp, as depicted in FIG. 5D, is employed in the channel flow path just prior to the channel region, which is open. Alternatively, a photon field, as may be provided by a laser commonly used in optical tweezers, may be employed to force the cells close to the surface. HAE cells may be obtained by routine biopsy and cultured. Before being loaded for ejection they must be disaggregated by conventional tissue culture methods and then suspended as individual cells.

The experiments may be conducted under conditions that permit cell division. The need for the preceding as well as the conditions required for this will be appreciated by one of ordinary skill. The controls with well plates are useful but not as critical as with the monocytes.

EXAMPLE 3
HAE Cell Array for Studying Individual Susceptibility to Mutagenesis as a Proxy for Carcinogenesis The method of the preceding example is adapted to permit exposing the arrayed HAE cells to chemical and other mutagens, such as heat and radiation. Genetic damage is measured at different times after the exposure is discontinued by routine methods, for example biochemical assaying of broken crosslinks and other damage to DNA. Differences in DNA repair enzyme genetics may be studied by comparing recovery (extent of reduction of damage) at various times after exposure. The well plate arrays remain useful as controls, and cells may be cultured in the well plates, or array cells may be removed and cultured, to determine whether there is actual appearance of dysplastic or neoplastic cells in subsequent cell generations after the exposure.

EXAMPLE 4
Cell Patterning

The method of Examples 1 and 2 is adapted to pattern basal squamous cells. Basal squamous keratinizing epithelial cells and squamous non-keratinizing epithelial cells are patterned on a nitrocellulose substrate functionalized as in Example 1. The pattern generated emulates the vermillion border of the lip. The patterned cells on the substrate are then immersed in a suitable culture medium, and studies are performed regarding the formation of a skin/non-keratinizing junction.

EXAMPLE 5
Acoustic Ejection of Lymphocytes from Blood onto an Epitope Array

Small, medium, and large lymphocytes are ejected by the methods of the preceding examples to form a clonal epitopic array. Two parallel, adjacent channels are constructed with differing widths and are appropriately designed to force the cells to be near the surface. The wider channel is about 15 $\mu$m wide to accommodate medium and large lymphocytes; the narrower channel is 10 $\mu$m wide to accommodate small lymphocytes. Small lymphocytes may be separated from large and medium lymphocytes by routine methods, or by acoustic ejection. An amount of energy barely sufficient to eject small lymphocytes is applied as all the lymphocytes in the mixture pass through one common channel (15 $\mu$m wide). The energy is applied to each lymphocyte, which is detected at the channel opening or aperture that forms the ejection region. The ejected lymphocytes may be ejected onto a substrate and washed into a petri dish or other container. Alternatively, the acoustic energy can be delivered to eject the droplet in a non-vertical trajectory so that the droplets land in a nearby container, such as a channel that is open on top and is sufficiently near the ejection channel.

The epitope array is a combinatorial tetrapeptide array formed from naturally occurring amino acids. Other epitopes are readily appreciated to exist both in proteins, as a result of non-primary structure, in peptidic molecules bearing haptens, and in other biomolecules such as peptidoglycans and polysaccharides. Only a small fraction of the approximately $10^{12}$ epitopes will be arrayed. Both T and B cells will bind these epitopes, by slightly different mechanisms, as will be readily appreciated. The tetrapeptide arrays can be made by various methods, for example by adaptation of solid phase peptide synthesis techniques to devices using focused acoustic ejection of reagents, as described in the copending application on combinatorial chemistry described above. As $1.6 \times 10^4$ different natural tetrapeptides exist, 16 1-cm$^2$ array areas (each containing 1000 array sites) must be available for synthesis of all the tetrapeptides and to maintain an appropriate density for allowing separation of individual cells.

Cells are spotted onto the array sites as rapidly as possible (thus the need for two channels to maintain single-file lines of cells in the channels despite the different sizes). When each of the 16,000 array sites has had a droplet ejected onto it, the arrays are washed to remove cells that do not bind the epitope at the deposition site. The arrays are imaged to determine which sites have bound a cell, and the cycle is repeated for sites not binding a cell, which are re-spotted. Immediately apprehended is that this process requires imaging of the array after washing, and must be automated. Automation of such a system is readily attainable, and invaluable information on clonal separation would be derived prior to completion of the project. Use of different types of epitopes would further extend the cataloguing.

EXAMPLE 6
Ejection of Bacteria to Select Transformed Bacteria

*E. coli* are transformed by routine methods to express pancytokeratin, a eukaryotic protein, by a construct that also causes expression and display of streptavidin on the cell surface. The cells are acoustically ejected onto a substrate biotinylated by routine methods, as described in the preceding Examples 1–5. The channel size must be adapted to bacterial dimensions (1 $\mu$m), but this is attainable by known microfabrication methods. Transformed cells will be specifically bound to the biotin cognate moiety by the marker moiety, streptavidin. Washing the substrate will remove cells that have not been transformed, leaving only transformed cells attached to the substrate.

We claim:

1. A method for ejecting a live cell from within a fluid onto a substrate surface without killing the cell, comprising delivering sufficient focused radiation to the fluid to eject the cell from the fluid, wherein prior to ejection the cell is located near the surface of the fluid and wherein upon ejection, the cell is contained in a droplet of said fluid.

2. The method of claim 1, wherein said focused radiation comprises focused acoustic radiation.

3. The method of claim 1, wherein a substrate is positioned over said fluid with a surface of the substrate facing the surface of the fluid, such that the cell-containing droplet is ejected onto the substrate surface.

4. The method of claim 1, wherein the fluid from which the cell is ejected is located within a fluidic channel having dimensions sufficient to permit the fluid and the cell to flow through the fluidic channel.

5. The method of claim 2, wherein a substrate is positioned over said fluid with a surface of the substrate facing the surface of the fluid, such that the cell-containing droplet is ejected onto the substrate surface.

6. The method of claim 2, wherein the fluid from which the cell is ejected is located within a fluidic channel having dimensions sufficient to pennit the fluid and the cell to flow through the fluidic channel.

* * * * *

UNITED STATES PATENT AND TRADEMARK OFFICE
CERTIFICATE OF CORRECTION

PATENT NO.    : 6,893,836 B2
DATED         : May 17, 2005
INVENTOR(S)   : Mitchell W. Mutz et al.

Page 1 of 1

It is certified that error appears in the above-identified patent and that said Letters Patent is hereby corrected as shown below:

Column 24,
Line 63, please delete the word "pennit" and replace it with the word -- permit --.

Signed and Sealed this

Sixth Day of September, 2005

JON W. DUDAS
*Director of the United States Patent and Trademark Office*